United States Patent [19]

Dordick et al.

[11] Patent Number: 5,449,613
[45] Date of Patent: Sep. 12, 1995

[54] REACTING AN ENZYME IN A NON-AQUEOUS SOLVENT BY ADDING A LYOPHILIZATE OF ENZYME AND SALT TO THE SOLVENT

[75] Inventors: Jonathan S. Dordick, Iowa City; Yuri Khmelnitsky, Coralville, both of Iowa; Douglas S. Clark, Oakland, Calif.

[73] Assignee: The University of Iowa Research Foundation, Iowa City, Iowa

[21] Appl. No.: 204,072

[22] Filed: Mar. 1, 1994

[51] Int. Cl.$^6$ .......................... C12P 1/00; C12N 9/00; C12N 9/14; C12N 9/02

[52] U.S. Cl. ..................................... 435/41; 435/183; 435/195; 435/189; 435/232; 435/233; 435/193

[58] Field of Search ............... 435/188, 187, 222, 198, 435/196, 134, 135, 41, 183, 195, 189, 232, 233, 193

[56] References Cited

PUBLICATIONS

Economou et al., Biotechnol. & Bioengineering, vol. 39, pp. 658–662, 1992.
Khmelnitsky et al., J. Am. Chem. Soc., 1994, 116, 2647–2648.
Ohtani et al., Kobuushi Ronbunshu, 1988, 45(9), 705–712.
Affleck et al., "Enzymatic Catalysis and Dynamics in Low–Water Environments," 89 Proc. Natl. Acad. Sci. 1100.
Dordick, "Enzymatic Catalysis in Monophasic Organic Solvents," 11 Enzyme Microb. Technol. 194 (1989).
Kanasawud et al., "Triglyceride Interesterification by Lipases. 3. Alcoholysis of Pure Triglycerides," 14 Enzyme Microb. Technol. 959 (1992).
Khmelnitsky et al., "Engineering Biocatalytic Systems in Organic Medial with Low Water Content," 10 Enzyme Microb. Technol. 710 (1988).
Otamari et al., "Effects on Ester Synthesis in Toluene by Immolilized Chymotrypsir, by Addition of Polymers to Reaction Medium," 13 Biotech. and Appld. Biochem. 521 (1991).
Ottolina et al., "Effect of the Enzyme Form on the Activity, Stability and Enantioselectivity of Lipoprotein Lipase in Toluene," 14 Biotech. Lttrs. 947 (1992).
Skrika-Alexopoulos et al., "Factors Affecting Enzyme Characteristics of Bilirubin Oxidase Suspensions . . . Solvents," 41 Biotech. and Bioeng. 887 (1993).
Vulfson et al., "L–Dopa Ester Synthesis Catalyzed by . . . Solvents," 12 Biotech. Lttrs. 597 (1990).
Yamane et al., "Intramolecular Esterification by Lipase Powder in Microaqueous Benzene: . . . Enzyme," 36 Biotech. and Bioeng. 1063 (1990).

*Primary Examiner*—David M. Naff
*Assistant Examiner*—Mike Meller
*Attorney, Agent, or Firm*—Thompson Hine & Flory

[57] ABSTRACT

A method for reacting an enzyme in a non-aqueous organic solvent is disclosed. The method comprises preparing a lyophilizate of a salt which activates the enzyme and an enzyme wherein the lyophilizate contains a weight ratio of salt to enzyme of at least 60% salt sufficient to activate the enzyme in an organic solvent. The method then calls for dispersion of the lyophilizate in a non-aqueous organic solvent in the presence of a substrate for the enzyme.

14 Claims, 2 Drawing Sheets

REACTING AN ENZYME IN A NON-AQUEOUS SOLVENT BY ADDING A LYOPHILIZATE OF ENZYME AND SALT TO THE SOLVENT

This invention was made with government support under Grant #DAAL03-91-G-0224 awarded by the Army Research Office and the Presidential Young Investigator Award awarded by the National Science Foundation. The government has certain rights in the invention.

BACKGROUND OF THE INVENTION

Enzymes catalyze a diverse array of reactions in non-aqueous media. However, their catalytic activities in organic solvents are often orders of magnitude lower than in aqueous solutions. Recent studies have shown that the catalytic performance of enzymes in organic solvents can be significantly improved by the incorporation of carbohydrates, polymers, or organic buffers into the dry catalyst, underscoring the important role of the enzymic microenvironment for catalysis in organic solvents. The present invention relates to the field of biocatalysis, in particular, enzymes functioning in non-aqueous media with low water content.

Non-aqueous enzymology has proven to be a convenient and versatile tool for fine organic synthesis. However, the denaturing effect or organic solvents, as compared to aqueous solutions, on the delicate structure of proteins often severely suppresses the catalytic performance of enzymes in organic solvents, thus, restricting the successful application of non-aqueous enzymology. In this case, the solvent alters the native conformation of the enzyme by disrupting hydrogen bonding and hydrophobic interactions thereby leading to reduced activity and stability. Certain enzymatic reactions, however, must be carried out in non-aqueous media to dissolve particular substrates and/or shift the thermodynamic equilibrium of the reaction toward the desired products. For that reason, a need has developed for a technique to conduct enzymatic reactions in non-aqueous solvents and maintain the stability of the enzymes.

The applicants have invented a process and a composition which activates enzyme catalysts in non-aqueous media. Presently, this method appears to be applicable with any class of enzyme.

SUMMARY OF THE INVENTION

It is now been found that the catalytic activities of enzymes in anhydrous organic solvents are dramatically increased when the enzymes are lyophilized in the presence of excess salts. One embodiment of the invention includes a lyophilized composition containing an enzyme and a salt in a weight ratio sufficient to activate the enzyme in an organic solvent.

A second embodiment of the invention is a method for reacting an enzyme in a non-aqueous media comprising the steps of first preparing a lyophilizate of an enzyme and a salt wherein the lyophilizate contains a salt in a weight ratio sufficient to activate the enzyme in an organic solvent and then dispersing the lyophilizate in a non-aqueous, organic solvent in the presence of a substrate for the enzyme.

DETAILED DESCRIPTION OF THE INVENTION

Figure 1:
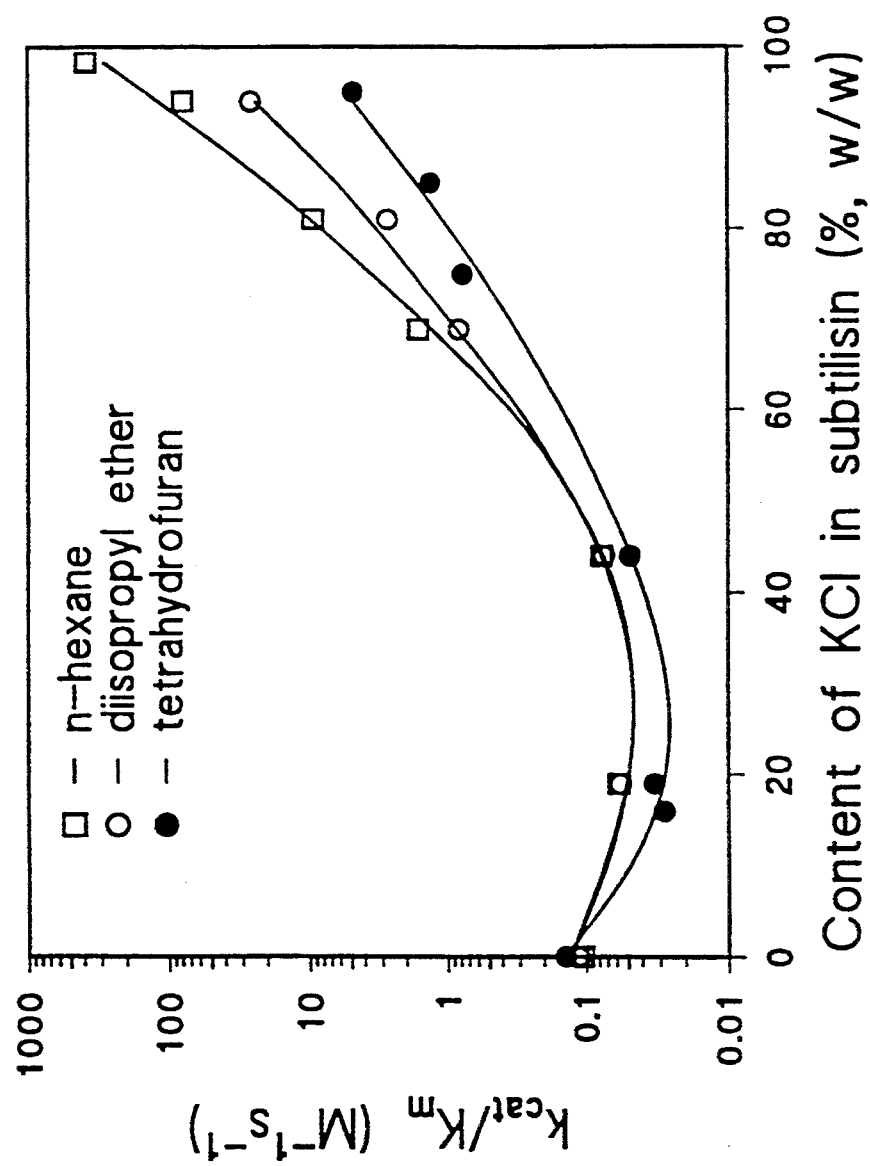
FIG. 1 is a graph demonstrating the catalytic activity of subtilisin in anhydrous organic solvents as a function of the KCl content in the dry catalyst.

The data in FIG. 1 and Table 1 show that the transesterification activity of subtilisin Carlsberg in anhydrous hexane is strongly dependent on the salt content of the lyophilized preparation and increases sharply when the salt content approaches 98%. For example, the value of $k_{cat}/K_m$ for transesterification of N-acetyl-1-phenylalanine ethyl ester with 1-propanol determined for the 98% KCl suspension ($390M^{-1}s^{-1}$) is over 3,750 times higher than that for the salt-free enzyme. Activation of subtilisin catalysis due to KCl occurs in a number of other widely different organic solvents, such as diisopropyl ether and tetrahydrofuran (FIG. 1), as well as acetonitrile, acetone, dioxane and toluene (not shown). The salt effect was not limited to subtilisin, specifically, the catalytic activity of α-chymotrypsin increased 50-fold when 95% (w/w) KCl was included in the lyophilized powder (Table 1).

TABLE 1

Effect of KCl as a Salt Matrix on Subtilisin Carlsberg and Chymotrypsin in Anhydrous Hexane*

| Enzyme | Salt Content (%, w/w) | $k_{cat}$ ($s^{-1}$) | $K_m$ (mM) | $k_{cat}/K_m$ ($M^{-1}s^{-1}$) |
|---|---|---|---|---|
| Subtilisin | 0 | 0.027 | 260 | 0.104 |
| " | 98 | 10.4 | 26.7 | 390 |
| Chymotrypsin | 0 | $4.2 \times 10^{-4}$ | 33.0 | 0.013 |
| " | 94 | $220 \times 10^{-4}$ | 33.0 | 0.67 |

*For the transesterification reaction of N-Acetyl-L-Phenylalanine Ethyl Ester with 0.85M 1-propanol.

The improvement of catalytic activity for both enzymes appears to be primarily a result of dramatically increased $k_{cat}$ rather than a decreased $K_m$ (Table 1). The activation effect depends on the enzyme and salt being intricately associated with one another, i.e., no activation was observed if the same concentration of KCl was added to the reaction mixture containing salt-free enzyme powder. Moreover, no change in activity was found when the concentration of phosphate in the KCl-based catalyst containing 5% enzyme was varied between 0 and 10%. Thus, catalytic activation does not depend upon the buffer properties of the enzyme salt matrix. This indicates that the salt effect is neither solvent nor salt specific and reflects a general fundamental feature of the enzymes-salt matrix.

One could speculate that the observed increase in catalytic activity results from reduced internal diffusion limitations due to substantial dilution of the biocatalyst and the enzyme-salt composite. However, internal diffusion is more likely to affect the salt-rich subtilisin powder than catalysis by the salt-free enzyme powder which is practically free of diffusional limitations. Thus, the intrinsic rate enhancement may be even somewhat higher than the observed activation. Furthermore, previous kinetic studies have shown that the activity in anhydrous organic solvents of subtilisin powder containing low amounts of buffer salts up to 35% (w/w) was unaffected by internal diffusion.

Figure 2:
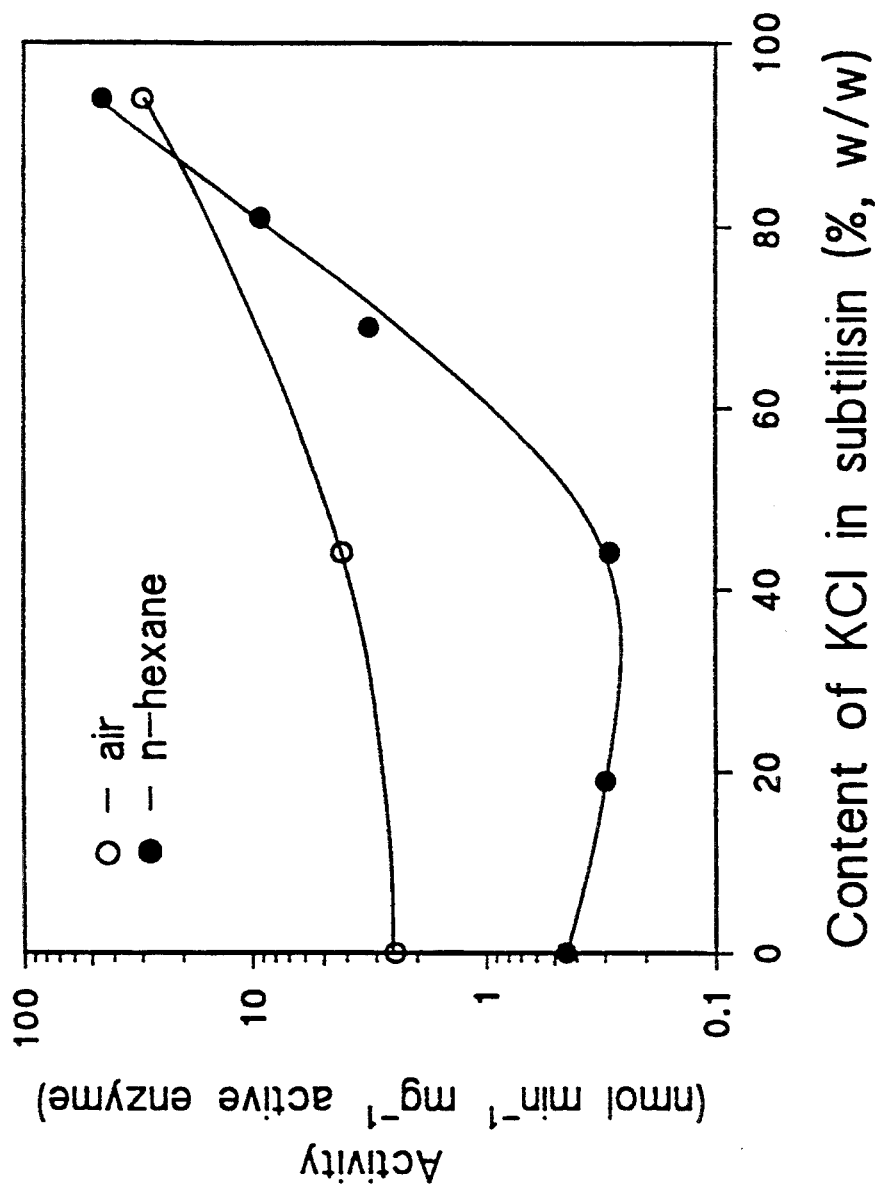
FIG. 2 is a graphic comparison of the catalytic activities of subtilisin as a function of KCl content in the dry catalyst in liquid (n-hexane) and gaseous (air) media.

The mechanism of salt-induced activation of enzyme activity in organic solvents may be due to at least two critical factors: the salt may protect the enzyme from direct inactivation by the organic solvent; or the salt may help to maintain the enzyme's native structure during lyophilization. In order to investigate the importance of these phenomena, activities of subtilisin/KCl catalyst were compared in both a liquid and gaseous medium; the latter presumably is inert towards enzyme molecules relative to the organic solvents. Hexane was chosen as a representative liquid medium, while air was used as the gaseous medium. Transesterification reactions of vinyl propionate with 1-butanol were performed. These substrates have solubility in hexane and sufficiently high vapor pressures to be present in the gas phase at 30° C. As depicted in FIG. 2, the presence of increasing amounts of KCl in the enzyme powder dramatically increases the activity of subtilisin in hexane —the enhancement upon adding 95% (w/w) KCl to the lyophilized powder was over 100-fold (an increase consistent with that obtained with N-acetyl-L-phenylanine ethyl ester for 95% (w/w) KCl ; compare FIGS. 1 and 2). In contrast, in the case of the gas phase reaction, the enhancement was less than 10-fold. If enzyme activation depends upon lyophilization, the observed magnitude of the rate enhancement should be the same in both media. Thus, the activation phenomenon observed in organic solvents cannot be explained solely in terms of a lyoprotectant effect of salts.

Although not wishing to be bound by any particular theory, the applicants hypothesize that the observed activation upon entrainment of the enzyme in a salt matrix is due to a protective effect afforded by the matrix against deactivation by direct contact with the organic solvent. At low salt contents, the solid catalyst particles are composed primarily of the lyophilized protein which forms a loosely structured environment. At higher salt contents, the catalyst particles presumably are more like that of free salt, which has a rigid structure that may protect the enzyme from the organic solvent. Furthermore, the salt matrix is highly polar and may help to maintain the native structure of the enzyme in organic medium.

Conventional lyophilization techniques can be used in the present invention to make the compounds of this invention. The enzyme, a salt and a buffer are combined in an aqueous solution. The buffer provides the optimum pH for the enzyme and can be in the lyophilizate in an amount of at least 1%. After the solution is prepared, it is frozen and freeze-dried in a conventional manner for approximately 48 hours. The lyophilized samples are stored over molecular sieves to eliminate any residual traces of water.

The resulting lyophilized enzyme-salt composition may be employed in any type of reaction in which enzymes are used in organic media. An example of a tranesterification reaction employing a lyophilized enzyme-salt composition is presented in Example 2 below. Typical examples of enzymatic reactions carried out in organic solvents include steroid oxidations; epoxidations; dehydrogenations; phenolic polymerizations; lignin depolymerization; esterification; acylation; peptide synthesis; and resolution of racemic mixtures.

This invention has been found to be particularly useful in synthetic reactions involving enzymes in organic solvents. Typical examples of these types of reactions include chiral ester synthesis by lipases, esterases and proteases; chiral lactone synthesis by lipases; synthesis of regioselective sugar ester derivatives via peroxidases, tyrosinases and laccases; synthesis of sugar based polymers (e.g., polyesters, polyacrylates, and polyacetylenes) by means of lipases and proteases coupled with chemical catalysts (e.g., chemoenzymatic synthesis); and the synthesis of chiral alcohols, aldehydes and ketones via alcohol dehydrogenases.

The activating ability of a salt appears to be effective with all classes of enzymes. These classes of enzymes, which can be stabilized for use in organic solvents, include hydrolases, isomerases, ligases, lyases, oxidoreductases and transferases. It has been discovered that hydrolases such as proteases, lypases and esterases are typically effective with this invention.

Because of the broad nature of this invention, most salts, such as sodium salts or potassium salts, are useful. Typically, the invention employs potassium salts, such as $KCl$, $KNO_3$, $K_2SO_4$, and $KF$. Organic salts have also been found to be useful in the compositions of this invention, and tetrabutyl ammonium chloride and $K^+CH_3COO^-$ have been found to be particularly useful.

The amount of salt used will vary with the nature of the enzyme and its reactivity in the solvent toward the substrate. The salt is generally present in the enzyme-salt composition in a ratio of at least 60% salt by weight. Preferably, the salt is employed in a ratio of at least 95% and, most preferably, in a ratio of 98%.

EXAMPLE 1

The following lyophilization procedure is exemplary of that used to create the compositions of this invention:

To produce a catalyst containing 94% salt, 1% potassium phosphate buffer and 5% subtilisin Carlsberg, all percentages given in weight per cent, an aqueous solution was prepared containing 100 ml of distilled water, 188 mg of salt, 2 mg of $KH_2PO_4$ and 10 mg subtilisin. 4M KOH was used to adjust the pH to 7.8. The resultant solution was frozen with liquid nitrogen and freeze-dried for 48 hours. Enzyme catalysts with other salt catalysts are prepared in essentially the same manner except that the salt/enzyme weight ratio is varied to achieve the desired salt content.

EXAMPLE 2

The following enzyme-catalyzed transesterification is exemplary of a typical enzyme-catalyzed reaction of this invention:

A reaction mixture containing 2.94 ml of n-hexane (stored over molecular sieves to eliminate traces of water), 10 mg lyophilized composition (containing the desired percentage of salt), 0.2 ml of n-propanol (stored over molecular sieves to eliminate traces of water), and 6.9 mg of N-acetyl-L-phenylalanine ethyl ester was prepared. Final concentrations of the reactants were 10 mM for N-acetyl-L-phenylalanine ethyl ester and 0.84 M for n-propanol. Next, the mixture was subjected to ultrasound treatment for 30 seconds in a standard laboratory sonicating bath to reduce the size of the catalyst particles, and the resultant suspension was incubated at 30° C. in an orbit shaker operating at 250 strokes/minute. At approximately every 1.5 to 2 hours, an aliquot of the reaction mixture was withdrawn from the reaction vial, centrifuged for 5 minutes at 10,000 rpm to separate the catalyst. The transparent supernatant was analyzed by gas chromatography to determine the concentration of the ester product. The transesterification reaction proceeds according to the following simplified scheme:

N-acetyl-L-phenylalanine ethyl ester + n-propanol →

-continued

N-acetyl-L-phenylalanine propyl ester + ethanol

Having described the invention in detail and by reference to preferred embodiments thereof, it will be apparent that modifications and variations are possible without departing from the scope of the invention defined in the appended claims.

What is claimed is:

1. A method for reacting an enzyme in a non-aqueous organic solvent comprising the steps of:
   preparing a lyophilizate of a salt which activates the enzyme and an enzyme wherein the lyophilizate contains a weight ratio of salt to enzyme of at least 60% salt sufficient to activate the enzyme in an organic solvent; and
   dispersing the lyophilizate in a non-aqueous organic solvent in the presence of a substrate for the enzyme.

2. The method of claim 1 wherein the enzyme is selected from the group consisting of hydrolases, isomerases, ligases, lyases, oxidoreductases and transferases.

3. The method of claim 2 wherein the enzyme is a hydrolase.

4. The method of claim 1 wherein the salt is selected from the group consisting of sodium salts and potassium salts.

5. The method of claim 4 wherein the potassium salt is selected from the group consisting of potassium chloride, potassium nitrate, potassium sulfate and potassium fluoride.

6. The method of claim 1 wherein the salt is selected from the group consisting of potassium acetate and tetrabutylammonium chloride.

7. The method of claim 1 wherein the salt to enzyme ratio in said lyophilizate is at least 95% salt.

8. The method of claim 7 wherein the salt to enzyme ratio in said lyophilizate is at least 98% salt.

9. The method of claim 8 wherein the enzyme is selected from the group consisting of hydrolases, isomerases, ligases, lyases, oxidoreductases and transferases.

10. The method of claim wherein the 1 lyophilizate contains at least 1% of a buffer salt in addition to the salt that activates the enzyme.

11. The method of claim 9 wherein said enzyme is subtilisin.

12. The method of claim 9 wherein said enzyme is alphachymotrypsin.

13. The method of claim 11 wherein said salt is potassium chloride.

14. The method of claim 12 wherein said salt is potassium chloride.

* * * * *

UNITED STATES PATENT AND TRADEMARK OFFICE
CERTIFICATE OF CORRECTION

PATENT NO. : 5,449,613
DATED : September 12, 1995
INVENTOR(S) : Dordick et al.

It is certified that error appears in the above-indentified patent and that said Letters Patent is hereby corrected as shown below:

Title page,
item [73] Assignee: before "The University of Iowa Research Foundation, Iowa City, Iowa" insert --The Regent of the University of California, Berkeley, Berkeley, California and--.

Signed and Sealed this

Twenty-fourth Day of September, 1996

*Attest:*

BRUCE LEHMAN

*Attesting Officer*     *Commissioner of Patents and Trademarks*